US011227669B2

(12) United States Patent
Nwankwo

(10) Patent No.: US 11,227,669 B2
(45) Date of Patent: Jan. 18, 2022

(54) COMPUTER AIDED DRUG RESISTANCE CALCULATOR CALCULATING DRUG RESISTANCE USING AMPRENAVIR AS A CASE STUDY

(71) Applicant: Norbert Ikechukwu Nwankwo, Elele (NG)

(72) Inventor: Norbert Ikechukwu Nwankwo, Elele (NG)

(73) Assignees: Norbert Ikechukwu Nwankwo, Anna, TX (US); Ngozika Tracey Nioku, Anna, TX (US)

( * ) Notice: Subject to any disclaimer, the term of this patent is extended or adjusted under 35 U.S.C. 154(b) by 0 days.

(21) Appl. No.: 14/311,247

(22) Filed: Jun. 21, 2014

(65) Prior Publication Data

US 2015/0370964 A1 Dec. 24, 2015

(51) Int. Cl.

| | |
|---|---|
| ***G16B 40/10*** | (2019.01) |
| ***G16B 40/00*** | (2019.01) |
| ***G16B 20/00*** | (2019.01) |
| ***G16B 20/50*** | (2019.01) |
| ***G16B 20/30*** | (2019.01) |

(52) U.S. Cl.

CPC ............. *G16B 40/10* (2019.02); *G16B 20/00* (2019.02); *G16B 20/30* (2019.02); *G16B 20/50* (2019.02); *G16B 40/00* (2019.02)

(58) Field of Classification Search

None

See application file for complete search history.

(56) References Cited

PUBLICATIONS

Gustchina et al. Proteins Structure, Function, and Genetics 10:325-339 (1991).*

Nwankwo et al. 32nd Annual International Conference of the IEEE EMBS Buenos Aires, Argentina, Aug. 31-Sep. 4, 2010, p. 1836-1839.*

Hoj et al. XVII International HIV Drug Resistance Workshop, Poster No. 113, 2008.*

Pozniak, A. et al., "British HIV Association (BHIVA) guidelines for the treatment of HIV-infected adults with antiretroviral therapy", 2001, HIV Medicine, 2:276-313, British HIV Association (BHIVA).

Cohen, C.J., et al., "A randomized trial assessing the impact of phenotypic resistance testing on antiretroviral therapy", 2002, AIDS, 16:579-588.

Cosic I., "Macromolecular bioactivity: is it resonant interaction between macromolecules?—Theory and applications", 1994, IEEE Transactions on Biomedical Engineering, 41:1101-1114.

Doliana, R., et al., "EMILINs interact with anthrax protective antigen and inhibit toxin action in vitro", 2008, Matrix Biology, 27:96-106.

Durant, J., et al., "Drug-resistance genotyping in HIV-1 therapy: the VIRAD APT randomised controlled trial", 1999, Lancet, 353:2195-2199.

Miller, V., et al., "Clinical and laboratory guidelines for the use of HIV-1 drug resistance testing as part of treatment management: recommendations for the European setting", 2001, AIDS, 15:309-320,The EuroGuidelines Group for HIV Resistance.

Fernandez, L., et al., "Amino acid sequence autocorrelation vectors and Bayesian-regularized genetic neural networks for modeling protein conformational stability: gene V protein mutants", 2007, Proteins: Structure, Function, and Bioinformatics, 67:834-852.

Flandre, P., et al., "Phenotypic susceptibility to didanosine is associated with antiviral activity in treatment-experienced patients with HIV-1 infection", J. Infectious Diseases, 2007, 195:392-398.

Gianotti, N., et al., "Comparison of a rule-based algorithm with a phenotype-based algorithm for the interpretation of HIV genotypes in guiding salvage regimens in HIV-infected patients by a randomized clinical trial: The mutations and salvage study", 2006, Clin. Infectious Diseases, 42:1470-1480.

Hanna. G. J., et al., "Clinical use of genotypic and phenotypic drug resistance testing to monitor antiretroviral chemotherapy", 2001, Clin. Infectious Diseases, 32:774 782.

Hirsch, M. S., et al., "Antiretroviral drug resistance testing in adult HIV-1 infection: 2008 recommendations of an international AIDS Society-USA panel", 2008, Clin. Infectious Diseases, 47:266-285.

Hoj, L., et al., "In silco identification of physiochemical properties at mutating positions relevant to reduced susceptibility to amprenavir", 2008, XVII International HIV Drug Resistance Workshop, Poster No. 113.

Kapetanovic, I.M., "Computer-aided drug discovery and development (CADDD): in silico-chemico-biological approach", 2008, Chem. Biol. Interact. 171: 165-176.

Nwankwo, N., et al., "A signal processing-based bioinformatics approach to assessing drug resistance: Human Immunodeficiency Virus as a case study", 2010, 32nd Annual International Congress of IEEE EMBS, p. 1836-1839.

Panel on Antiretroviral Guidelines for Adults and Adolescents. "Guidelines for the use of antiretroviral agents in HIV-1-infected adults and adolescents", 2011, Department of Health and Human Services, 2011.

Perez-Elias, M.J., et al., "Phenotype or virtual phenotype for choosing antiretroviral therapy after failure: a prospective, randomized study", 2003, Antiviral Therapy, 8:577-584.

(Continued)

*Primary Examiner* — Michael L Borin

(74) *Attorney, Agent, or Firm* — JWIP & Patent Services, LLC; Jacob G. Weintraub, Esq.

(57) ABSTRACT

Signal Processing-based Computer-Aided Drug Resistance Calculator (CARDC) has been proposed [14]. The result of the drug resistances obtained then demonstrated very small margin. It was noted that more than one amino acids parameter is engaged in one mutation. It became necessary to further apply CARDC on studies which have information on both mutations in the target protein and the amino acids parameters involved. Amprenavir, an anti-HIV/AIDS that has been approved by FDA has been studied and information regarding mutations and amino acids parameters are available [12]. CARDC is therefore applied on these mutations and amino acids parameters presented.

12 Claims, 17 Drawing Sheets

Specification includes a Sequence Listing.

(56) References Cited

PUBLICATIONS

Porter, K., et al., Cascade Collaboration, "Determinants of survival following HIV-1 seroconversion after the introduction of HAART", 2003, Lancet, 362:1267-1274.

Ravela, J., et al., "HIV-1 protease and reverse transcriptase mutation patterns responsible for discordances between genotypic drug resistance interpretation algorithms", 2003, JAIDS Journal of Acquired Immune Deficiency Syndromes, 33:8-14.

Rhee, S-Y., et al. "Human immunodeficiency virus reverse transcriptase and protease sequence database", 2003, Nucleic Acids Research, 31:298-303.

Thompson, M. A., et al., "Antiretroviral treatment for adult HIV infection 2010 Recommendations of the International Aids Society—USA panel", 2010, JAMA, 304:321-333.

Torti, C., et al., "A randomized controlled trial to evaluate antiretroviral salvage therapy guided by rules-based or phenotype-driven HIV-1 genotypic drug-resistance interpretation with or without concentration-controlled intervention the resistance and dosage adapted regimens (RADAR) study", 2005, Clin. Infectious Diseases, 40:1828-1836.

Vaidyanathan, P. P., "Genomics and proteomics: a signal processors tour", 2004, IEEE Circuits and Systems Magazine, 4:6-29.

Veljkovic, V., et al., "Characterization of conserved properties of hemagglutinin of H5N1 and human influenza viruses: possible consequences for therapy and infection control", 2009, BMC Structural Biology, 9:21-30.

Veljkovic, V., et al., "Identification of hemagglutinin structural domain and polymorphisms which may modulate swine H1N1 interactions with human receptor", 2009, BMC Structural Biology, 9:62-72.

Vercauteren, J., et al., "Algorithms for the interpretation of HIV-1 genotypic drug resistance information", 2006, Antiviral Res., 71:335-342.

Ziermann, R., et al., "A mutation in Human Immunodeficiency Virus type 1 protease, N88S, that causes in vitro hypersensitivity to amprenavir", 2000, Journal of Virology, 74:4414-4419.

Browne, C. A., et al., "The isolation of peptides by high-performance liquid chromatography using predicted elution positions", 1982, Analytical Biochem., 124:201-208.

Nwankwo, N., "Designing and developing therapeutic interventions in the bioinformatics era", 2013, Drug Des., 2:1-2.

Nwankwo, N., "A digital signal processing-based bioinformatics approach to identifying the origins of HIV-1 non B subtypes infecting US Army personnel serving abroad", 2013, Current HIV Res., 11:271-280.

Nwankwo, N., "Signal processing-based bioinformatics methods for characterisation and identification of bio-functionalities of proteins", 2012, Thesis Documents, De Monfort University, p. 1-231.

Veljkovic, I., et al., "Is it possible to analyze DNA and protein sequences by the methods of digital signal processing?", 1985, IEEE Trans Biomedical Eng., BME-32:337-341.

Murugan, N., Karbowski, L. and Persinger, M. (2015) Cosic's Resonance Recognition Model for Protein Sequences and Photon Emission Differentiates Lethal and Non-Lethal Ebola Strains: Implications for Treatment. Open Journal of Biophysics, 5, 35-43. doi: 10.4236/ojbiphy.2015.51003.

Emmanuel D. Levy, Subhajyoti De, and Sarah A. Teichmann. PNAS Dec. 11, 2012 109 (50) 20461-20466; https://doi.org/10.1073/pnas.1209312109.

Emmanuel D. Levy, Subhajyoti De, and Sarah A. Teichmann. PNAS Dec. 11, 2012 109 (50) 20461-20466; https://doi.org/10.1073/pnas.1209312109-Supporting Information.

Cosic I, Pirogova E. Bioactive peptide design using the Resonant Recognition Model. Nonlinear Biomedical Physics. 2007;1:7. doi: 10.1186/1753-4631-1-7.

Suria Valdés García and José Luis Hernández-Cáceres. Studying Protein kinases PKCζ and PKMζ with the Resonant Recognition Model. Implications for the study of Memory Mechanisms. Revista Cubana de Informática Médica 2017:9(2)121-134.

* cited by examiner

> Consensus sequence (Stanford):

PQITLWQRPLVTIKIGGQLKEALLDTGADDTVLEEMNLPGRWKPK

MIGGIGGFIKVRQYDQILIEICGHKAIGTVLVGPTPVNIIGRNLLTQ

IGCTLNF SEQ ID NO:23

>Mutant N88K

PQITLWQRPLVTIKIGGQLKEALLDTGADDTVLEEMNLPGRWKPK

MIGGIGGFIKVRQYDQILIEICGHKAIGTVLVGPTPVNIIGRKLLTQI

GCTLNF SEQ ID NO:24

>Random 1

PISPIETVPVKLKPGMDGPKVKQWPLTEEKIKALVEICTEMEKEGKI
SKIGPENPYNTPVFAIKKKDSTKWRKLVDFRELNKRTQDFWEVQL
GIPHPAG SEQ ID NO:25

Fig. 1

COMPUTER AIDED DRUG RESISTANCE CALCULATOR CALCULATING DRUG RESISTANCE USING AMPRENAVIR AS A CASE STUDY

In accordance with 37 C.F.R. 1.821-1.824, a Sequence Listing accompanies this application. The Sequence Listing is incorporated herein by reference in its entirety and is to be entered into the application in its entirety.

BACKGROUND OF THE INVENTION

Incorporating drug resistance testing into the patient management profiles remains vital in the management of diseases including HIV/AIDS and as a result, guidelines have also been issued by various organisations. More vital though, is calculating the drug resistance. Drug resistance assay techniques such as Genotyping, Phenotyping and also a combination of the two including VirtualPhenotype have been employed. However, results obtained by these procedures have been found to be discordant and difficult to interpret. This has made choice of drug for patients' management difficult.

SUMMARY OF THE INVENTION

We have earlier proposed a Bioinformatics device called Computer-Aided Drug Resistant Calculator (CARDC). This tool is a cost saving, computer-assisted, signal processing-based approach which integrates the amino acid information of the proteins in order to computationally calculate the degree of resistance. It is devoid of laboratory-based experimental procedures and also, predictive outcomes. It rather calculates drug resistance.

BRIEF DESCRIPTION OF THE DRAWINGS

FIG. 1. Example of the sequences analysed showing Consensus sequence from Stanford, Mutant N88K (bold letter) and Random 1 (R1).

DETAILED DESCRIPTION OF THE INVENTION

Figure 2:
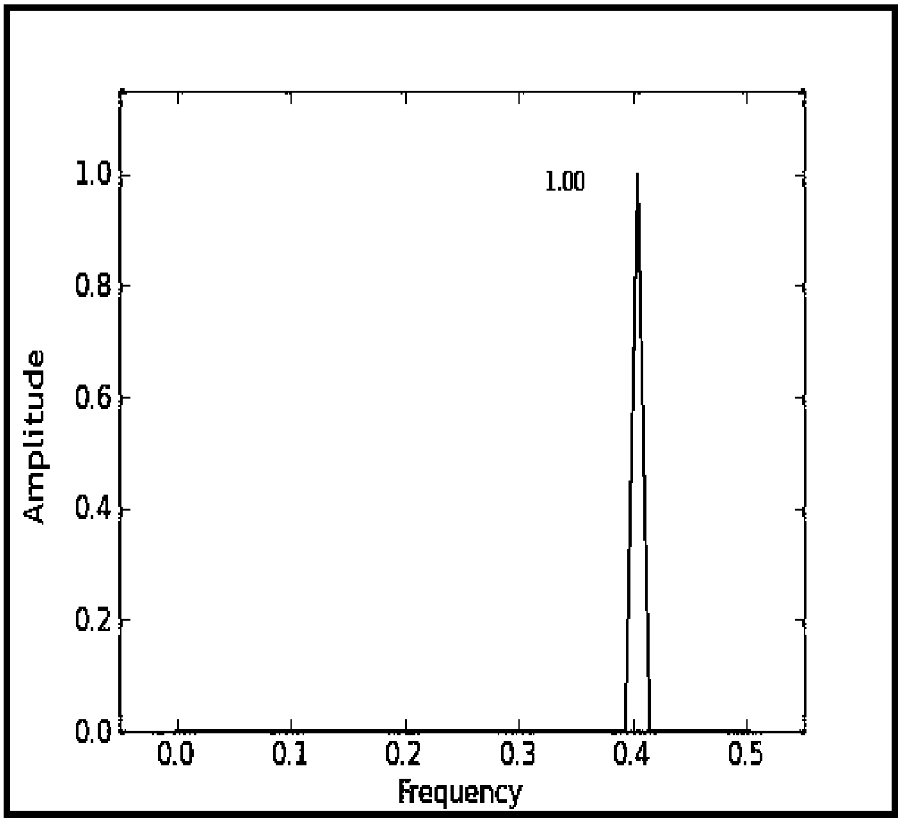
FIG. 2. CS of all mutations at Position 10 using amino acids parameter ROBB760107 showing the Consensus Frequency at 0.4043 and amplitude of 1.0.

There have been to incorporate drug resistance testing into patient management profiles especially in the field of HIV/AIDS since drug resistance has been the major cause of treatment failure [15]. Drug Resistance associated with HIV/AIDS as well as the viral replicative ability have help make HIV/AIDS disease incurable [11], [26]. HIV/AIDS treatment has therefore become a life-long activity. This is against the fact that since 1997, a combination of large number of anti-retroviral agents are being utilised to manage HIV/AIDS in the name of Highly Active Anti-retroviral Therapy (HAART) [17]. To minimise HIV/AIDS drug resistance, treatment guidelines, which are acknowledged and approved as fundamental outline for the HIV/AIDS management have been issued [1], [6], [15], [20].

Laboratory-based assessment of drug resistance has been declared labour-intensive, expensive, time and resources consuming [14]. They are also prone to more errors as unwanted components such as unanticipated micro-organisms could be introduce during microbiological assays. Also operating systems could be faulty and measurements could be inaccurate. Computational approaches have been recognised to be more rational as they are fast, resource saving [13], limits human involvement and therefore reduced error.

Genotypic-resistance assay technique is a computational procedure for assessing drug resistance which utilises amino acids information. It has been recognised to be better than other procedures [5], [15]. Genotypic-resistance testing technique involves sequencing of the relevant protein residues so as to identify mutations that are responsible for reduced susceptibility [10], [15]. Other computational approaches which have been employed in evaluating drug susceptibility or insensitivity include Phenotype assay technique [15], [21]. In Phenotypic-resistance assay technique, drug susceptibility is measured using different concentrations so as to determine the drug strength that inhibits expected responses [10], [15], [21]. Furthermore, a combination of these procedures have also been utilised to better assess resistances offered by drugs [2], [16]. However, these techniques have been found to encounter major obstacles as results derived by these approaches have been found to be difficult to interpret [15]. Although some algorithms have been invented to help reading results [8], [9], [21], [25], yet discordant outcomes are still being obtained [18]. These setbacks have been the major source of concern for medical practitioners in the application of these techniques.

We have earlier proposed a signal processing-based Bioinformatics device technique, which integrates the amino acid information of the proteins for the purposes of computationally assessing the degree resistance. This Bioinformatics device is called Computer-Aided Drug Resistant Calculator (CARDC) [14]. It assesses the degree resistance without involving the resource-consuming laboratory-based experimental procedures.

It has been reported that for each mutation in the entire protein residue, more than one amino acids parameter may be involved. We then concluded that aggregation of the resistance offered by all the mutations using amino acids parameters engaged is needed to obtain the complete resistance presented by the drug target proteins.

One major benefit of employing Signal Processing-based technique in protein sequence analysis is that it translates the alphabetic codes of the amino acids sequences into numerical values by means of the amino acids parameters [3]. It further processes these numerical sequences in order to provide biological information about the proteins including resistance offered when exposed to the drugs. About 565 amino acids parameters have been discovered [12]. Each amino acids parameter describes biological functionality including drug mechanisms of action and resistance. As a result, this Signal Processing-based Computer-Aided Drug Resistant Calculator calculates drug resistance rather than predict them.

However, it has been recognised that each mutation in the entire sequence is governed by one or more amino acids parameter [12]. As a result, we noted that aggregation of the resistance presented by individual mutation in respect of all the amino acids parameter engaged is required to obtain total drug resistance [14]. In essence, complete resistance offered by single drug can be accurately calculated through aggregation of the result obtained using all the amino acids parameters involved in each mutation. This is to incorporate all the amino acids parameters involved in each mutation.

To obtain resistance offered by single mutation based on particular amino acids parameter, investigation into the mechanism of action, hence resistance at atomic level is need. This is to help identify the physiochemical (hydrophobicity, Acidity, and others), structural (Helix, Alpha, Beta and others) or any other properties involved. Unfortunately, only very few drugs have been investigated for this purpose. Such investigations have been carried out on Amprenavir [12].

Using CARDC, resistances offered by the mutations in HIV target protein residues against Amprenavir as shown in (Table. 1) which were preliminarily studied [12] are obtained and the outcomes are correlated. The result is found to be promising that it is applied to calculate the Amprenavir-induced resistance by the protein. The CARDC calculated resistance is tentative derived as 5.86% which seems to suggest that Amprenavir could be administered to this patient. The results are presented in the subsequent sections.

1 METHODS

1.1 Materials

The consensus amino acids sequences of the HIV Protease enzyme, the target proteins for the Amprenavir are retrieved from Stanford University Release Notes [19]. Corresponding amino acids sequences for the mutations earlier studied [12] and shown in Table 1 are then constructed from the consensus sequences. By means of our CARDC, these sequences are analysed using amino acids parameters ascribed to the positions of the mutations as demonstrated in Table 1. As a control, 10 random sequences are generated and studied with amino acids parameter referred to as Ra which stands for Solvent-accessible reduction ratio [7]. FIG. 1 is the demonstration of the Stanford consensus sequence, the mutated and randomly generated sequences used in this study. In the case of Ko amino acids parameter, more mutations than identified are studied.

1.2 Information Spectrum Method (ISM)

The Computer-Aided Drug Resistance Calculator (CADRC) is used to calculate the drug activities (susceptibility and resistance) of the Amprenavir based on the initial studies [12]. CADRC is a Digital Signal Processing-based device. It employs Information Spectrum Method (ISM) procedures, which have been utilised by numerous researchers [4], [14], [23], [24]. ISM procedures are briefly described below.

The ISM procedures include:

1.2.1 Translation of the Alphabetic Code of the Protein Residues into Numerical Values.

The alphabetic code of amino acids sequences for both the Consensus and the mutated protein residues are first converted into numerical values using all amino acids scale engaged. In this study, the 22 amino acids parameters which are used in the preliminary studies [12] are engaged to calculate the resistance offered by the HIV against Amprenavir.

1.2.2 Application of the Discrete Fourier Transform (DFT)

These numerical sequences (signals) are processed using discrete Fourier transform (DFT). Absolute values of the complex DFT which is presented as a plot called Informational Spectrum (IS) discloses the information embedded in the protein residues. Here, the y-axis (Amplitude) signifies the contribution in terms of drug activities (susceptibility or resistance) from each sequence against Amprenavir while the x-axis (Frequency) indicates the position of the HIV protein residue at which Amprenavir interacts. To better characterise the differences in the amplitude, the y-axis is scaled in such a manner that the sum total of all the amplitudes equals 1.00. The drug susceptibility is then represented by the amplitude while the difference between the highest amplitude that signifies the most susceptible and others is the drug resistance.

1.2.3 Common Informational Spectrum (CIS)

Common Informational Spectrum (CIS) is then performed. This is used to obtain the common position of interaction by all the Amprenavir-induced mutations, called the Consensus Frequency (CF). CIS is the point-wise multiplication of the DFT-processed signal from all the sequences studied, which provides common information about them [4], [23], [24] [22]. This procedure which the CADRC engages is applied to all the constructed sequences arising from the Amprenavir-induced mutations and the amino acids parameters engaged as studied [12] and shown in Table 1.

The results obtained with various amino acids parameters are plotted and correlated first correlated with the results obtained preliminarily [12]. These outcomes are presented in the subsequent section.

2 EXEMPLIFICATIONS

Twenty two (22) Amino acids parameters are engaged in the calculation of the Amprenavir-induced resistance using mutations previously studied [12]. The results are presented below.

Figure 3:
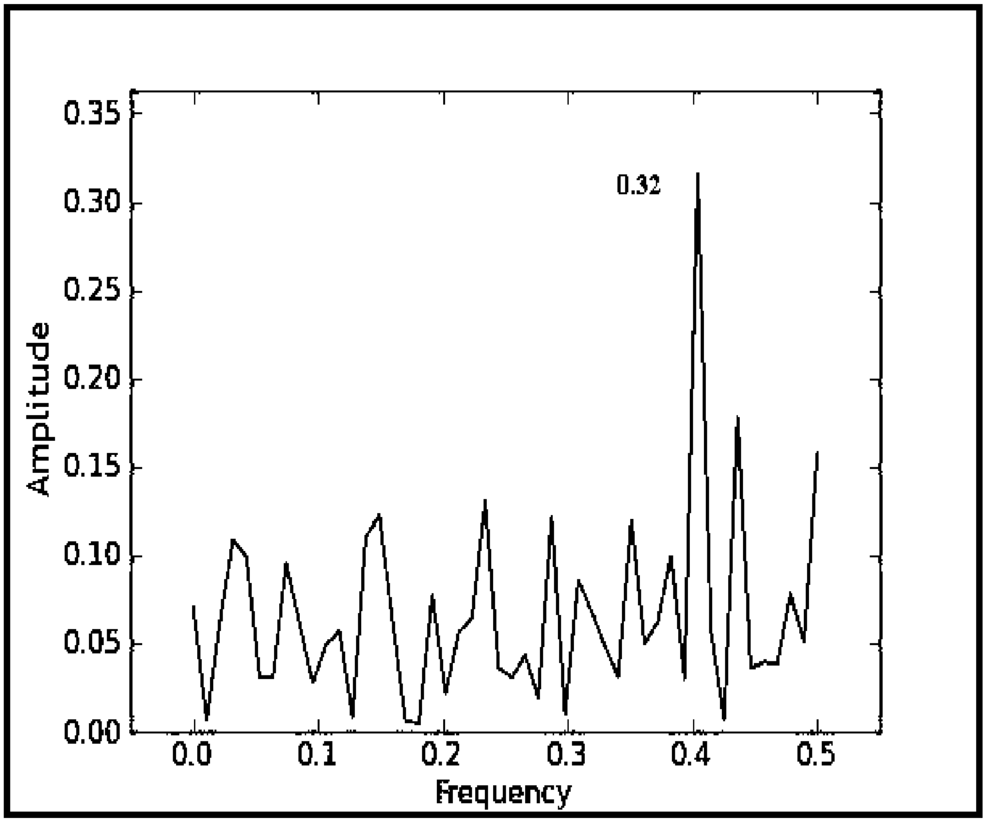
FIG. 3. IS of L10W using amino acids parameter ROBB760107 showing maximal amplitude of 0.32 at the Consensus Frequency (CF=0.4043) which appears to suggest 0% resistance as shown in Table 3.
Figure 4:
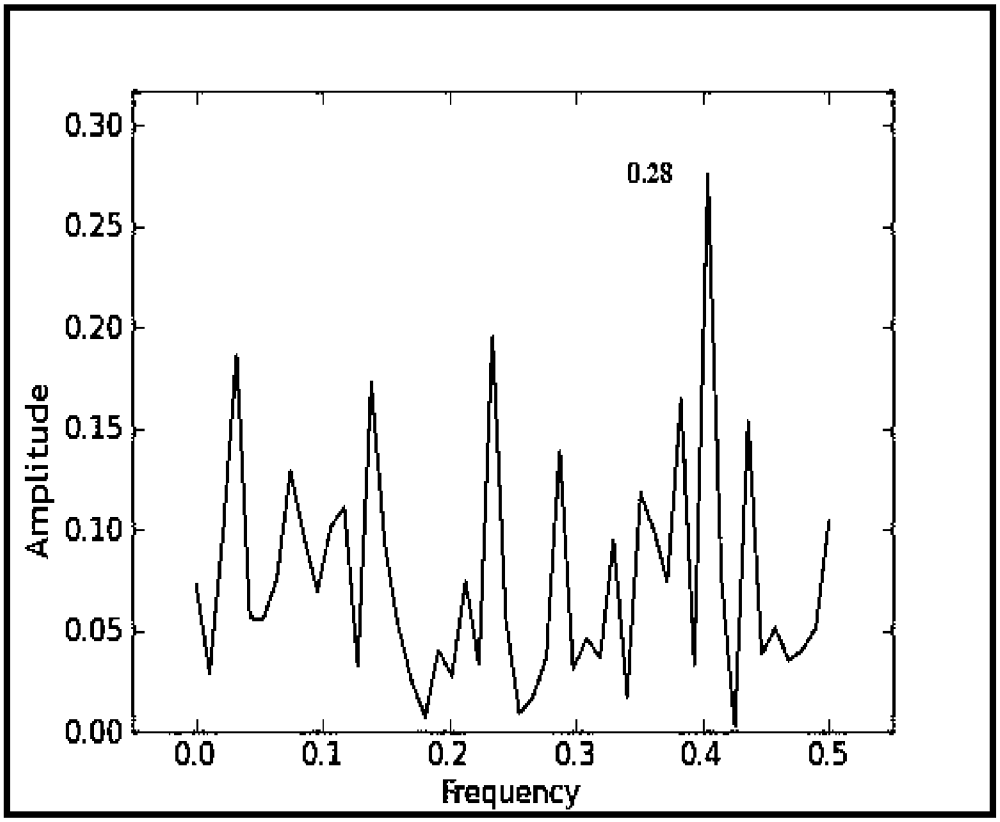
FIG. 4. IS of L10P using amino acids parameter ROBB760107 showing minimal amplitude of 0.28 at the Consensus Frequency (CF=0.4043) which appears to suggest 12% resistance as shown in Table 3.

2.1 Amino Acid Parameter:

The Consensus Frequency of all the mutations engaged by amino acids parameters, ROBB760107 are obtained by means of the CADRC. The Common Informational Spectrum (CIS) of the protein residues analysed with the CADRC using amino acids parameter ROBB760107 is presented in FIG. 2. The Consensus Frequency (CF) is at 0.4043 with amplitude of 1.00. The informational Spectrum (IS) of mutation (L10W) reveals amplitude of 0.32 (FIG. 3) which is the maximum as demonstrated on Table 3. This seems to signify that it is susceptible (offers no resistance) to Amprenavir unlike mutation L10P which has amplitude of 0.28 suggesting 12% resistance (FIG. 4 and Table 3). The resistance calculated from all mutations using the amino acids parameter ROBB760107 is 5.0% (Table 3).

2.2 Amino Acid Parameter: BROC820102

Figure 5:
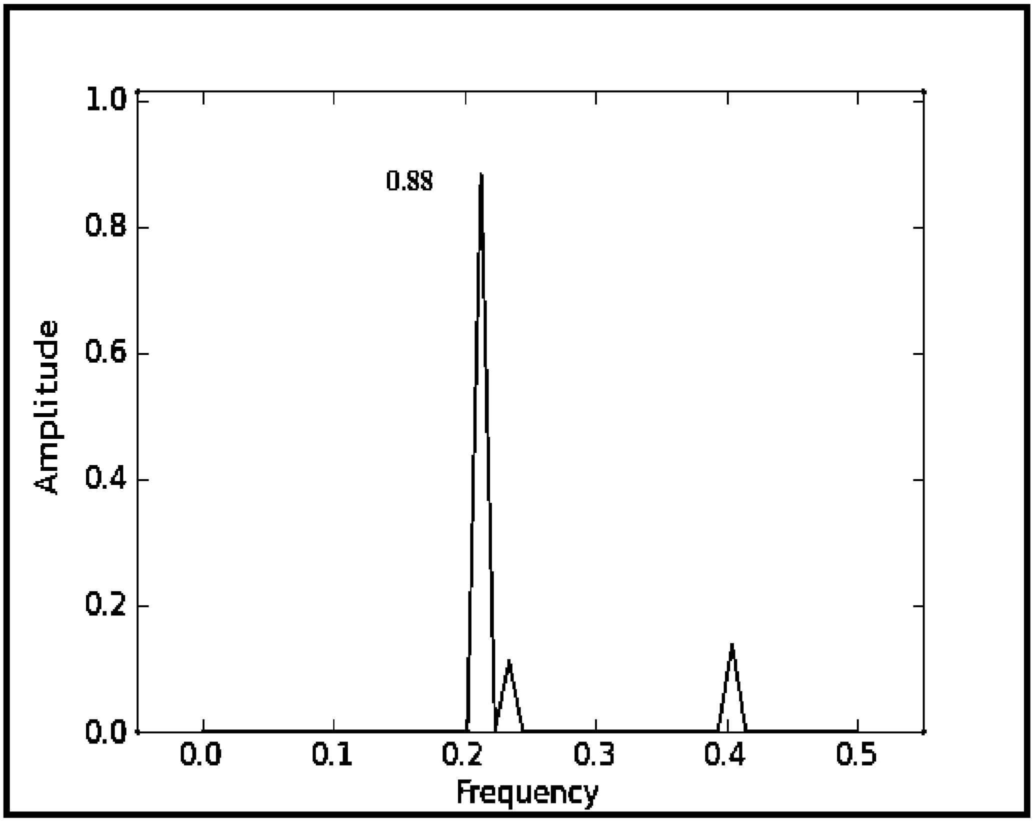
FIG. 5. CS of all mutations at Position 50 using amino acids parameter BROC820102 showing Consensus Frequency at 0.2128 with Amplitude of 0.88.
Figure 6:
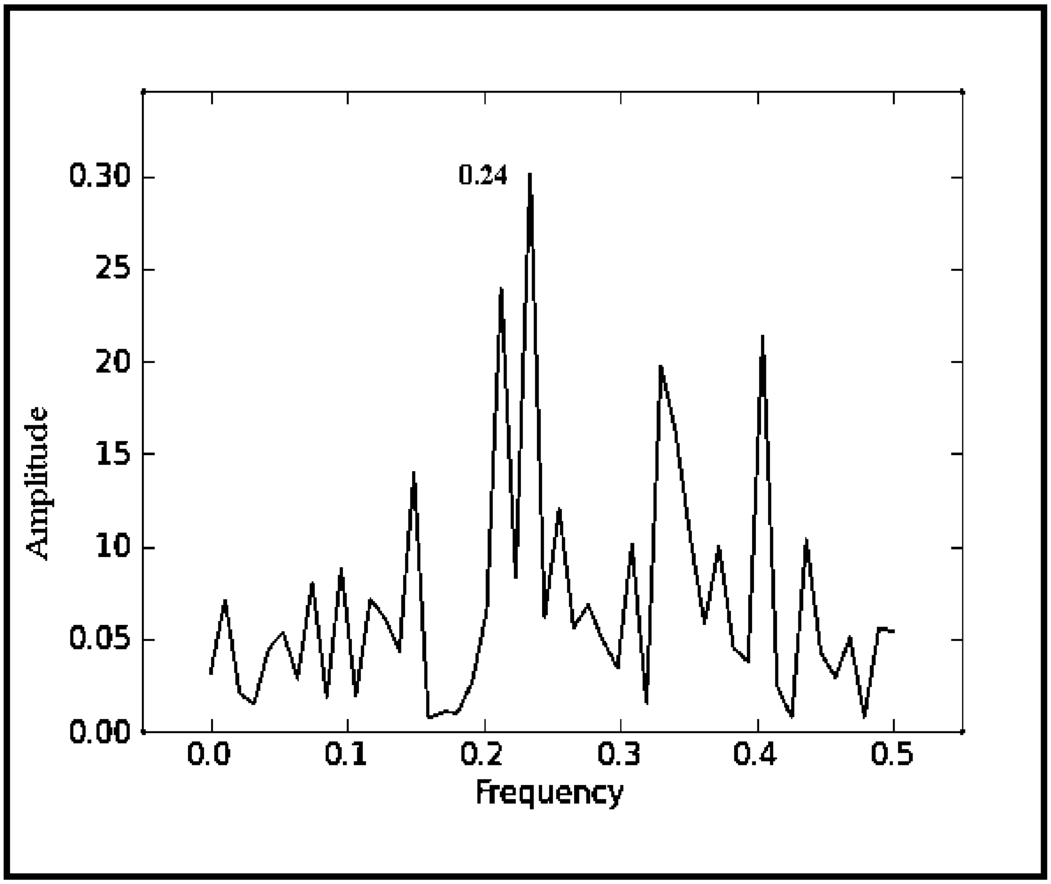
FIG. 6. IS of I50W for BROC820102 showing minimal amplitude of 0.24 at the Consensus Frequency (CF=0.2128) which appears to suggest 23% resistance as shown in Table 5.
Figure 7:
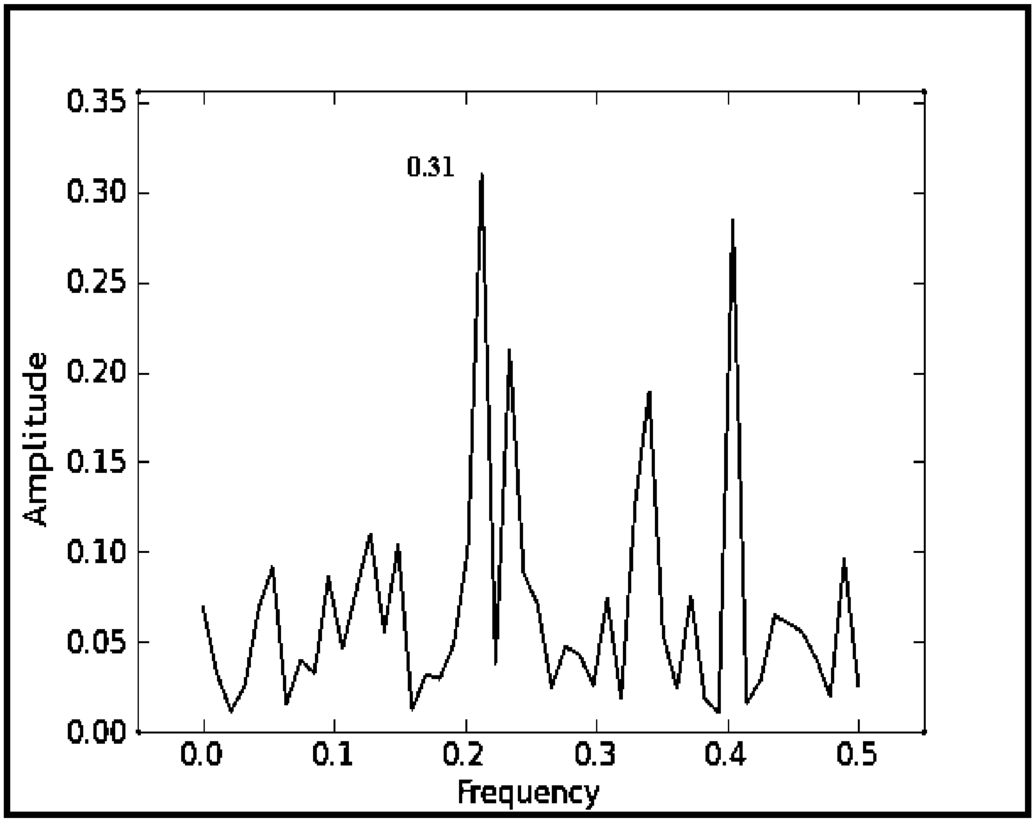
FIG. 7. IS of I50E for BROC820102 showing maximal amplitude of 0.31 at the Consensus Frequency (CF=0.2128) which appears to suggest 0% resistance as shown in Table 5.

The CIS of the analysis of the protein sequences analysed by means of CARDC using amino acids parameter BROC820102 which is displayed in FIG. 5 demonstrated a CF of 0.2128 with amplitude of 0.88. One of the least resistant strain (I50E) has amplitude of 0.31 which suggest 0% resistance (FIG. 7 and Table 5). Unlike I50E, contribution by mutation I50W is 23% resistance. It has amplitude of 0.24 (FIG. 6).

2.3 Amino Acid Parameter: TSAJ990101

Figure 8:
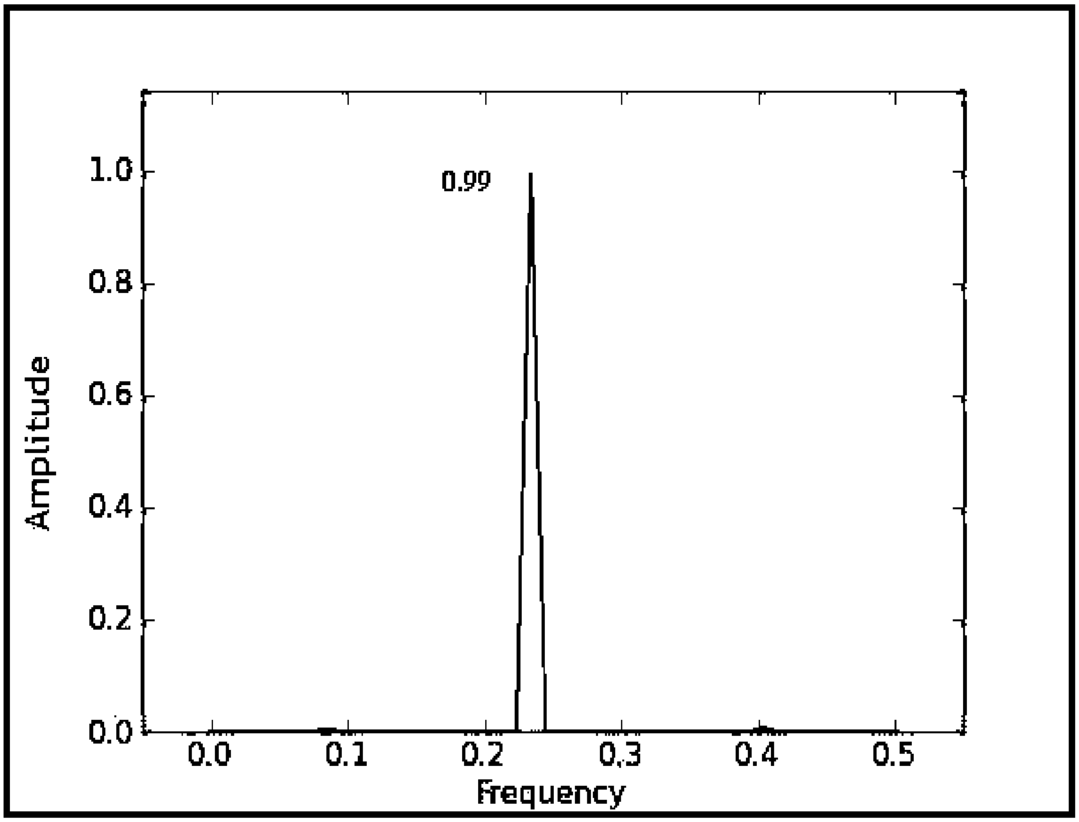
FIG. 8. CS of all mutations at Position 84 using amino acids parameter TSAJ990101 showing the Consensus Frequency at 0.234 with Amplitude of 0.99.
Figure 9:
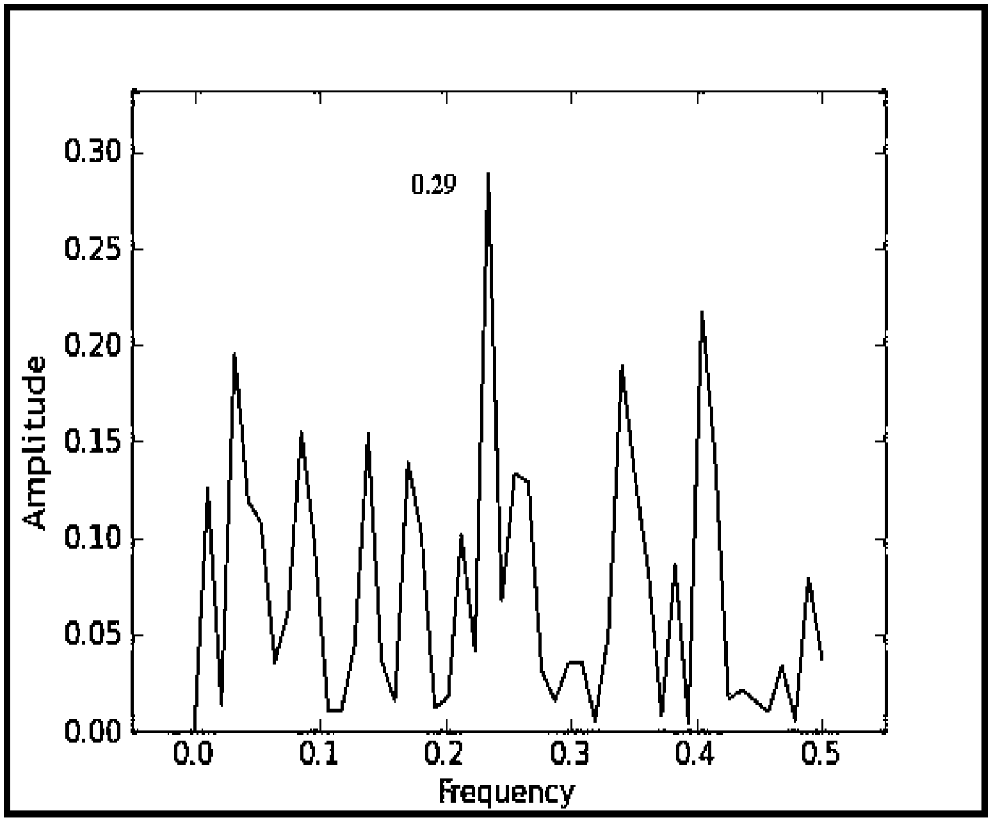
FIG. 9. IS of I84W for TSAJ990101 showing maximal amplitude of 0.29 at the Consensus Frequency (CF=0.234) which appears to suggest 0% resistance as shown in Table 8.
Figure 10:
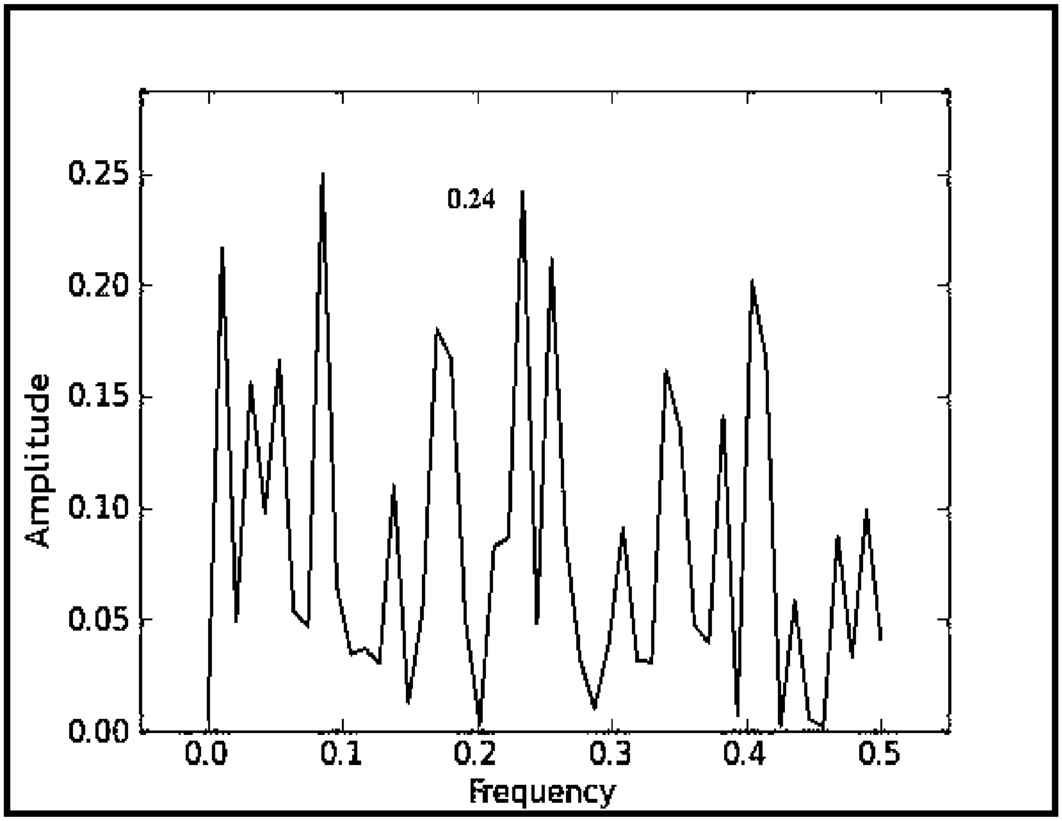
FIG. 10. IS of I84A for TSAJ990101 showing minimal amplitude of 0.24 at the Consensus Frequency (CF=0.234) which appears to suggest 17% resistance as shown in Table 8.

The CIS of the protein residues studied with the amino acids parameter TSAJ990101 displayed a CF with amplitude of 0.99 at 0.234 as shown in FIG. 8. The IS of two mutations, namely I84W and I84A (FIGS. 9 and 10) demonstrated least and maximum resistances, respectively. While I84W has nil resistance with amplitude of 0.29, I84A offered resistance of 17% with amplitude of 0.24.

2.4 Amino Acid Parameter: Ra

Figure 11:
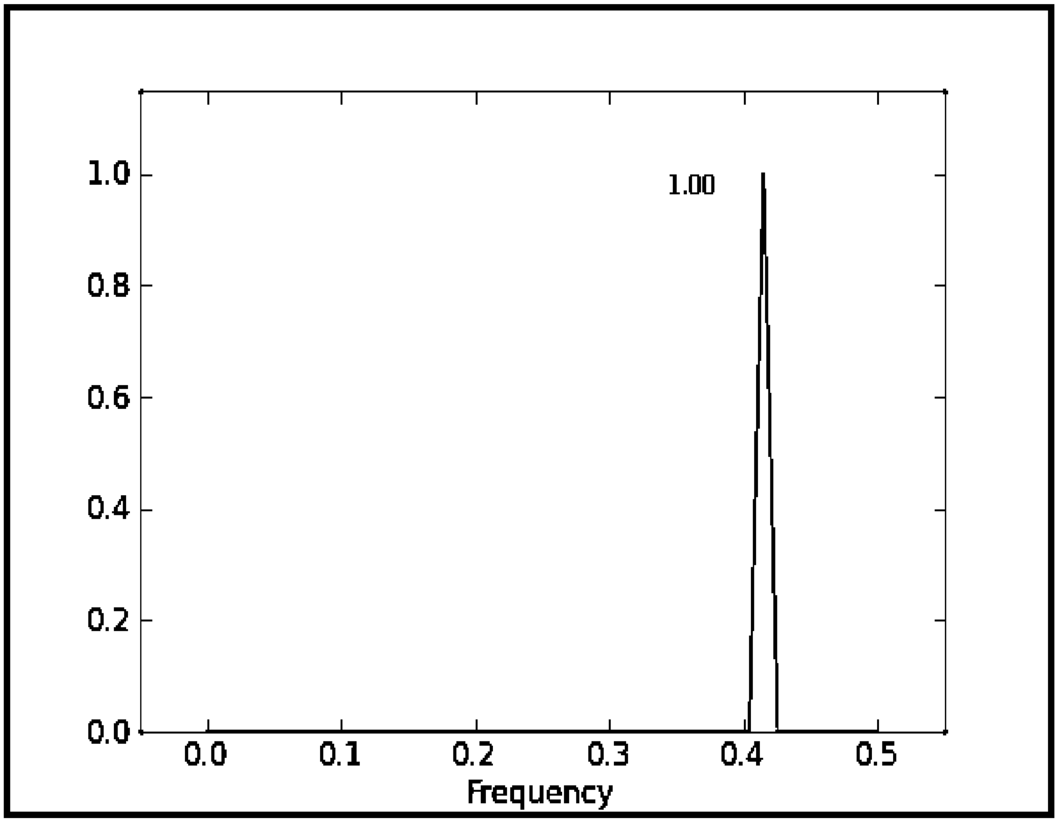
FIG. 11. CS of all mutations at Position 88 using amino acids parameter Ra showing the Consensus Frequency at 0.4149 (position 22) with Amplitude of 1.0.
Figure 12:
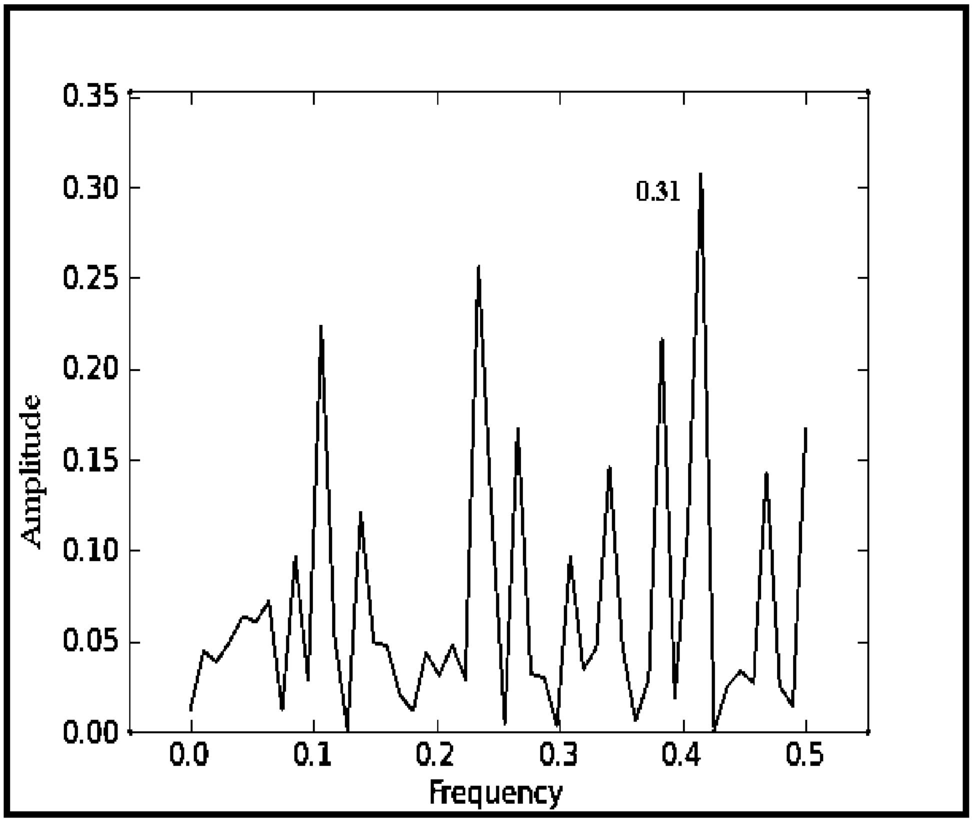
FIG. 12. IS of Mutant N88A for Ra showing maximal amplitude of 0.31 at the Consensus Frequency (CF=0.4149) which appears to suggest 100% Susceptibility as shown in Table 9.
Figure 13:
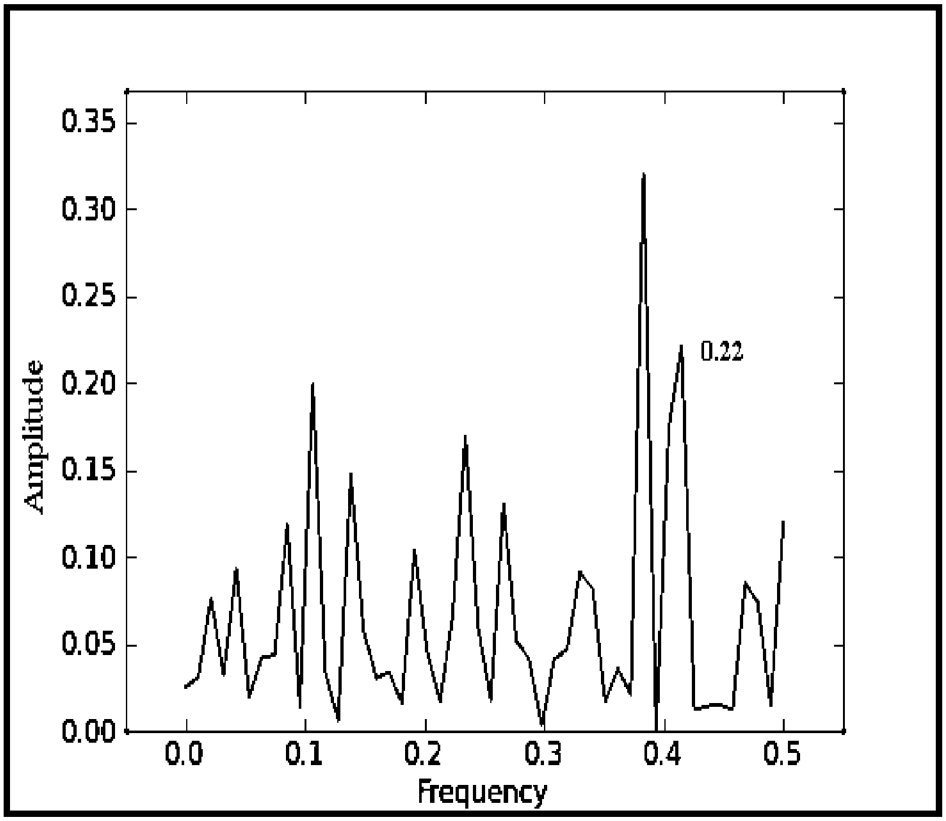
FIG. 13. IS of N88F for Ra showing minimal amplitude of 0.22 at the Consensus Frequency (CF=0.4149) which appears to suggest 29% resistance as shown in Table 9.
Figure 14:
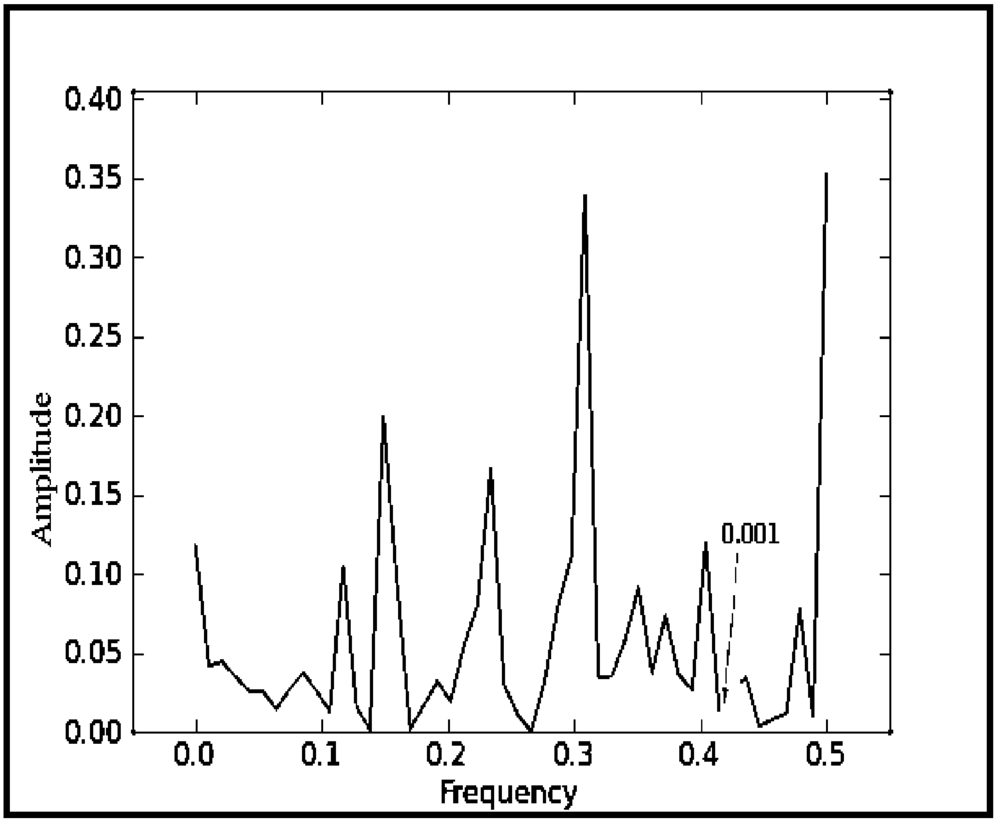
FIG. 14. IS of Random Sequence 1 using Ra Parameter showing insignificant amplitude of 0.00 at the CF at 0.4149 which appears to suggest 100% resistance as shown in Table 9.
Figure 15:
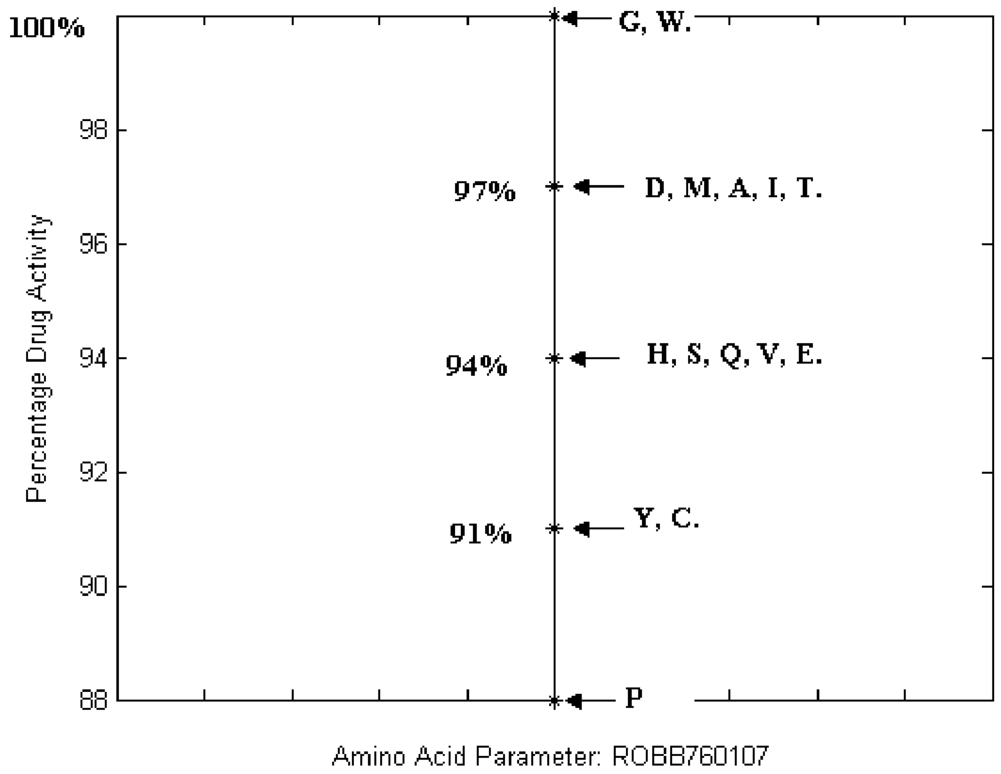
FIG. 15. Plot of the Drug Activity of the Amprenavir displayed by the Mutations using Amino Acid Parameter ROBB760107.
Figure 16:
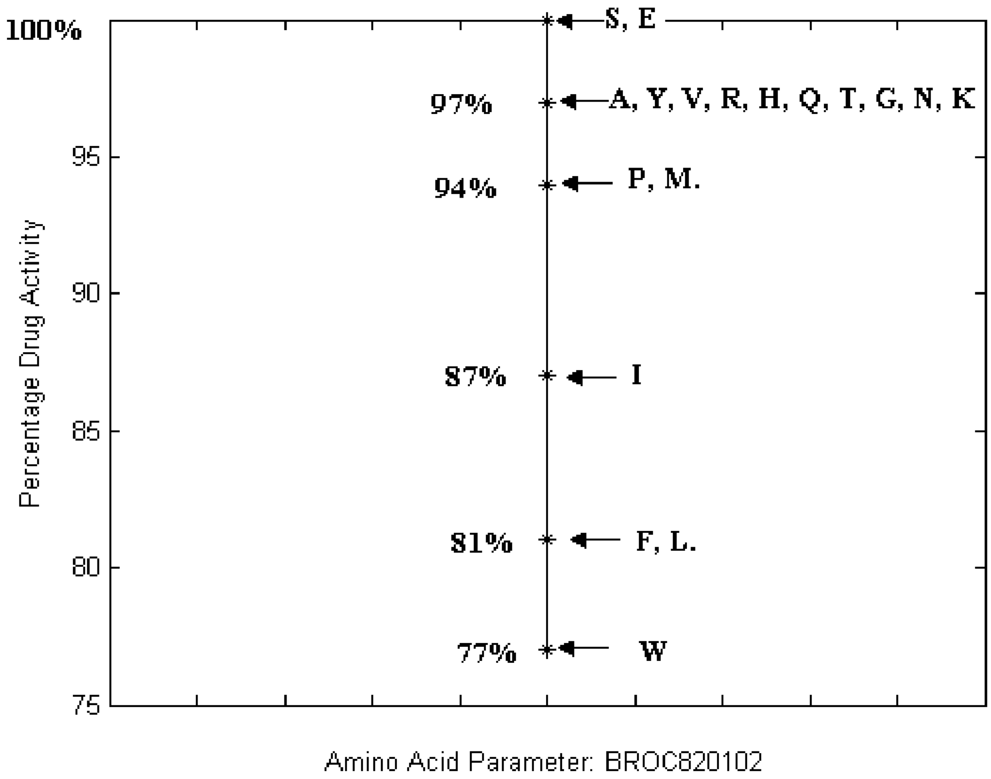
FIG. 16. Plot of the Drug Activity of the Amprenavir displayed by the Mutations using Amino Acid Parameter BROC820102.
Figure 17:
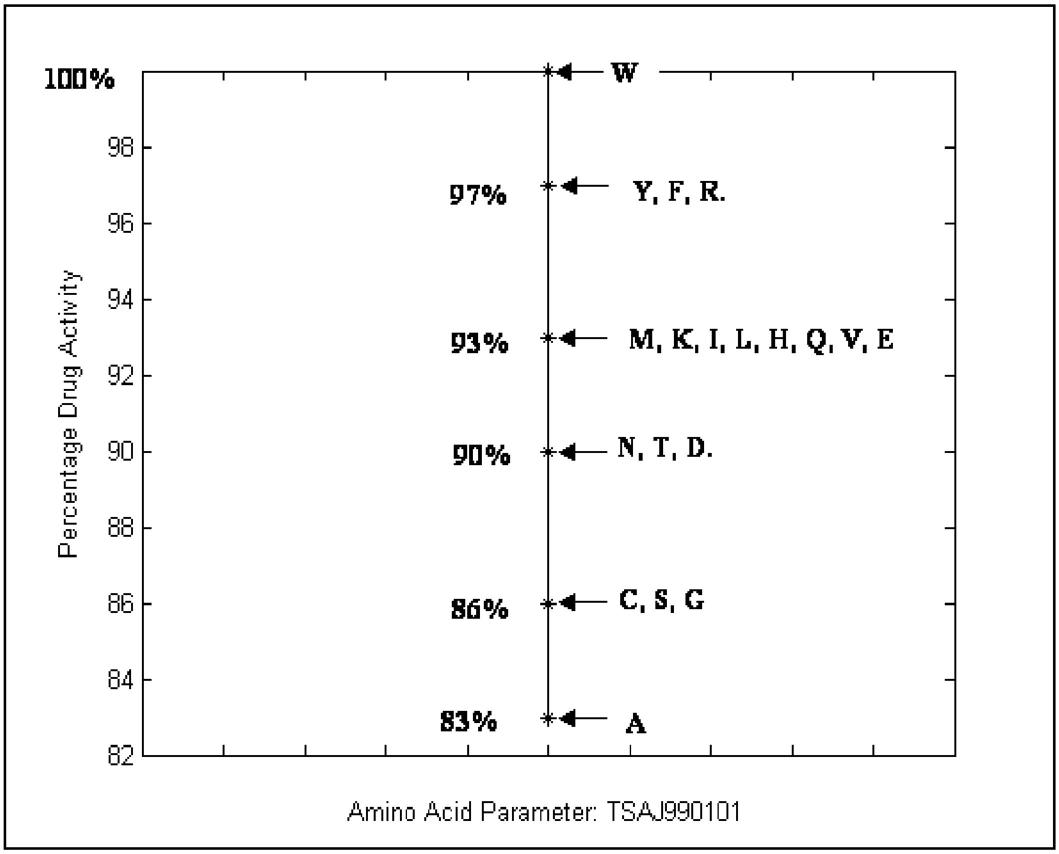
FIG. 17. Plot of the Drug Activity of the Amprenavir displayed by the Mutations using Amino Acid Parameter TSAJ990101P.

In the case of the amino acids parameter, 10 randomly generated amino acids sequences are included. The CIS revealed in FIG. 11 demonstrated a CF at 0.4149 with amplitude of 1.0. While the most resistant strain (N88F) has amplitude of 0.22 which suggests 29% resistance (13 and Table 9), the most susceptible has amplitude of (N88A) has amplitude of 0.31 which appears to demonstrate nil resistance (FIG. 12 and Table 9). Random sequence 6 has amplitude of 0.00 at 0.4149 (FIG. 14 and Table 9).

The amplitudes, percentage susceptibilities and resistances of the amino acids sequences analysed by means of CARDC using various amino acids parameters are displayed in Tables 2-10.

Using the results obtained here, the CARDC-processed susceptibility achieved by the sequences engaged with three amino acids parameters are plotted and correlated with preliminary studies [12]. The plots are displayed as ROBB760107 FIG. (15), BROC820102 FIG. (16), and TSAJ990101P FIG. (17). The result correlated well with the results in preliminary experiment [12] such that CARDC is further used to calculate the Amprenavir-induced resistance and the results are displayed in Table 1.

TABLE 1

Calculated Resistance Against Amprenavir by HIV as studied in [12].

| S/No | Position | Amino Acid Parameter | Mutations displayed | Average Resistance % |
|---|---|---|---|---|
| 1 | 10 | KANM800103 | VWYMQG (SEQ ID NO: 1) | 0.43% |
| 2 | 10 | NAKH900102 | AGQVTYWMH (SEQ ID NO: 2) | 11.46% |
| 3 | 10 | RACS820113 | QSTVMWHYCNG (SEQ ID NO: 3) | 4.64% |
| 4 | 10 | ROBB760107 | GWDMAITHSXQVEYCP (SEQ ID NO: 4) | 5.00% |
| 5 | 32 | ARGP8201 | QGTHAMVDPYIW (SEQ ID NO: 5) | 0.00% |
| 6 | 33 | CHAM830105 | WQYHMEIVTGPA (SEQ ID NO: 6) | 5.38% |
| 7 | 33 | GARJ730101 | WPMQVIYGD (SEQ ID NO: 7) | 6.00% |
| 8 | 33 | Ko | IVFWLMAHEGCYQTPRSNPK (SEQ ID NO: 8) | 6.15% |
| 9 | 46 | ROBB760109 | MAVLEGKWQRFSHYDNP (SEQ ID NO: 9) | 5.35% |
| 10 | 50 | BROC820102 | WFLIPMAYVRHQTGSNKEC (SEQ ID NO: 10) | 6.26% |
| 11 | 54 | FASG760102 | YLAVIWHMSQETCR (SEQ ID NO: 11) | 1.43% |
| 12 | 54 | RACS820105 | GAQTESDCLVFMYHW (SEQ ID NO: 12) | 9.46% |

TABLE 1-continued

| Calculated Resistance Against Amprenavir by HIV as studied in [12]. | | | | |
|---|---|---|---|---|
| S/No | Position | Amino Acid Parameter | Mutations displayed | Average Resistance % |
| 13 | 54 | VASM830102 | TSPCRLAMGEVWDFYNQKP (SEQ ID NO: 13) | 4.8% |
| 14 | 54 | QIAN880103 | VIWEMQDP (SEQ ID NO: 14) | 6.56% |
| 15 | 82 | NAKH920103 | LSETVGDQFKCMIYHW (SEQ ID NO: 15) | 9.53% |
| 16 | 84 | TSAJ990101 | WYFRMKILHQVENPTDCSAG (SEQ ID NO: 16) | 8.11% |
| 17 | 84 | VINM940104 | WVYHMQGT (SEQ ID NO: 17) | 5.56% |
| 18 | 88 | CEDJ970105 | VIHYMQA (SEQ ID NO: 18) | 3.80% |
| 19 | 88 | CHAM810101 | GQMWVIYER (SEQ ID NO: 19) | 3.27% |
| 20 | 88 | Ra | IVFWLMAHEGCYQTPRSNPK (SEQ ID NO: 20) | 13.81% |
| 21 | 88 | ROSM880103 | GQMWVIYER (SEQ ID NO: 21) | 6.60% |
| 22 | 90 | ANDN920101 | VIGLETAQSMAYHWDNPKR (SEQ ID NO: 22) | 5.35% |
| | | Average Resistance | | 5.86% |

TABLE 2

| Calculated Resistance in Position 10 using amino acids parameter: RACS820113 | | | | |
|---|---|---|---|---|
| S/No | Mutant | Amplitude | Susceptibility % | Resistance % |
| 1 | Q | 0.39 | 98.00% | 2.00% |
| 2 | S | 0.39 | 98.00% | 2.00% |
| 3 | V | 0.38 | 95.00% | 5.00% |
| 4 | T | 0.38 | 95.00% | 5.00% |
| 5 | M | 0.38 | 95.00% | 5.00% |
| 6 | W | 0.34 | 85.00% | 15.00% |
| 7 | H | 0.39 | 98.00% | 2.00% |
| 8 | Y | 0.40 | 100.00% | 0.00% |
| 9 | C | 0.38 | 95.00% | 5.00% |
| 10 | N | 0.38 | 95.00% | 5.00% |
| 11 | G | 0.38 | 95.00% | 5.00% |
| | Average | | 95.36% | 4.64% |

TABLE 3

| Calculated Resistance in Position 10 using amino acids parameter: ROBB760107. | | | | |
|---|---|---|---|---|
| S/No | Mutant | Amplitude | Susceptibility % | Resistance % |
| 1 | G | 0.32 | 100.00% | 0.00% |
| 2 | W | 0.32 | 100.00% | 0.00% |
| 3 | D | 0.31 | 97.00% | 3.00% |
| 4 | M | 0.31 | 97.00% | 3.00% |
| 5 | A | 0.31 | 97.00% | 3.00% |
| 6 | I | 0.31 | 97.00% | 3.00% |
| 7 | T | 0.31 | 97.00% | 3.00% |
| 8 | H | 0.30 | 94.00% | 6.00% |
| 9 | S | 0.30 | 94.00% | 6.00% |
| 10 | Q | 0.30 | 94.00% | 6.00% |
| 11 | V | 0.30 | 94.00% | 6.00% |
| 12 | E | 0.30 | 94.00% | 6.00% |
| 13 | Y | 0.29 | 91.00% | 9.00% |

TABLE 3-continued

| Calculated Resistance in Position 10 using amino acids parameter: ROBB760107. | | | | |
|---|---|---|---|---|
| S/No | Mutant | Amplitude | Susceptibility % | Resistance % |
| 14 | C | 0.29 | 91.00% | 9.00% |
| 15 | P | 0.28 | 88.00% | 12.00% |
| | | Average | 95.00% | 5.00% |

TABLE 4

| Calculated Resistance in Position 46 using amino acids parameter: ROBB760109. | | | | |
|---|---|---|---|---|
| S/No | Mutant | Amplitude | Susceptibility % | Resistance % |
| 1 | M | 0.27 | 90.00% | 10.00% |
| 2 | A | 0.27 | 90.00% | 10.00% |
| 3 | V | 0.28 | 93.00% | 7.00% |
| 4 | L | 0.28 | 93.00% | 7.00% |
| 5 | E | 0.27 | 90.00% | 10.00% |
| 6 | G | 0.30 | 100.00% | 0.00% |
| 7 | K | 0.28 | 93.00% | 7.00% |
| 8 | W | 0.28 | 93.00% | 7.00% |
| 9 | Q | 0.27 | 93.00% | 7.00% |
| 10 | R | 0.29 | 97.00% | 3.00% |
| 11 | F | 0.28 | 93.00% | 7.00% |
| 12 | S | 0.29 | 97.00% | 3.00% |
| 13 | H | 0.28 | 93.00% | 7.00% |
| 14 | Y | 0.29 | 97.00% | 3.00% |
| 15 | D | 0.29 | 97.00% | 3.00% |
| 16 | N | 0.30 | 100.00% | 0.00% |
| 17 | P | 0.30 | 100.00% | 0.00% |
| | | Average | 94.65% | 5.35% |

TABLE 5

| Calculated Resistance in Position 50 using amino acids parameter: BROC820102. | | | | |
|---|---|---|---|---|
| S/No | Mutant | Amplitude | Susceptibility % | Resistance % |
| 1 | W | 0.24 | 77.00% | 23.00% |
| 2 | F | 0.25 | 81.00% | 19.00% |
| 3 | L | 0.25 | 81.00% | 19.00% |
| 4 | I | 0.27 | 87.00% | 13.00% |
| 5 | P | 0.29 | 94.00% | 6.00% |
| 6 | M | 0.29 | 94.00% | 6.00% |
| 7 | A | 0.30 | 97.00% | 3.00% |
| 8 | Y | 0.30 | 97.00% | 3.00% |
| 9 | V | 0.30 | 97.00% | 3.00% |
| 10 | R | 0.30 | 97.00% | 3.00% |
| 11 | H | 0.30 | 97.00% | 3.00% |
| 12 | Q | 0.30 | 97.0% | 3.00% |
| 13 | T | 0.30 | 97.00% | 3.00% |
| 14 | G | 0.30 | 97.00% | 3.00% |
| 15 | N | 0.30 | 97.00% | 3% |
| 16 | K | 0.30 | 97.00% | 3.00% |
| 17 | S | 0.31 | 100.00% | 0.00% |
| 18 | E | 0.31 | 100.00% | 0.00% |
| 19 | C | 0.30 | 97.00% | 3.00% |
| | | Average | 93.74% | 6.26% |

TABLE 6

| Calculated Resistance in Position 54 using amino acids parameter: FASG760102. | | | | |
|---|---|---|---|---|
| S/No | Mutant | Amplitude | Susceptibility % | Resistance % |
| 1 | Y | 0.25 | 100.00% | 0.00% |
| 2 | L | 0.25 | 100.00% | 0.00% |
| 3 | A | 0.25 | 100.00% | 0.00% |
| 4 | V | 0.25 | 100.00% | 0.00% |
| 5 | I | 0.25 | 100.00% | 0.00% |
| 6 | W | 0.25 | 100.00% | 0.00% |
| 7 | H | 0.25 | 100.00% | 0.00% |
| 8 | M | 0.25 | 100.00% | 0.00% |
| 9 | S | 0.25 | 100.00% | 0.00% |
| 10 | E | 0.25 | 100.00% | 0.00% |
| 11 | T | 0.25 | 100.00% | 0.00% |
| 12 | R | 0.24 | 96.00% | 4.00% |
| 13 | Q | 0.23 | 92.00% | 8.00% |
| 14 | C | 0.23 | 92.00% | 8.00% |
| | | Average | 98.57% | 1.43% |

TABLE 7

| Calculated Resistance in Position 54 using amino acids parameter: RACS820105. | | | | |
|---|---|---|---|---|
| S/No | Mutant | Amplitude | Susceptibility % | Resistance % |
| 1 | G | 0.25 | 76.00% | 24.00% |
| 2 | A | 0.28 | 85.00% | 15.00% |
| 3 | Q | 0.28 | 85.00% | 15.00% |
| 4 | T | 0.29 | 88.00% | 12.00% |
| 5 | E | 0.29 | 88.00% | 12.00% |
| 6 | S | 0.30 | 91.00% | 9.00% |
| 7 | D | 0.30 | 91.00% | 9.00% |
| 8 | C | 0.30 | 91.00% | 9.00% |
| 9 | V | 0.31 | 94.00% | 6.00% |
| 10 | F | 0.31 | 94.00% | 6.00% |
| 11 | Y | 0.32 | 97.00% | 3.00% |
| 12 | H | 0.32 | 97.00% | 3.00% |
| 13 | W | 0.33 | 100.00% | 0.00% |
| | | Average | 9.54% | 9.46% |

TABLE 8

| Calculated Resistance in Position 84 using amino acids parameter: TSAJ990101. | | | | |
|---|---|---|---|---|
| S/No | Mutant | Amplitude | Susceptibility % | Resistance % |
| 1 | W | 0.29 | 100.00% | 0.00% |
| 2 | Y | 0.28 | 97.00% | 3.00% |
| 3 | F | 0.28 | 97.00% | 3.00% |
| 4 | R | 0.28 | 97.00% | 3.00% |
| 5 | M | 0.27 | 93.00% | 7.00% |
| 6 | K | 0.27 | 93.00% | 7.00% |
| 7 | I | 0.27 | 93.00% | 7.00% |
| 8 | L | 0.27 | 93.00% | 7.00% |
| 9 | H | 0.27 | 93.00% | 7.00% |
| 10 | Q | 0.27 | 93.00% | 7.00% |
| 11 | V | 0.27 | 93.00% | 7.00% |
| 12 | E | 0.27 | 93.00% | 7.00% |
| 13 | N | 0.26 | 90.00% | 10.00% |
| 14 | T | 0.26 | 90.00% | 10.00% |
| 15 | D | 0.26 | 90.00% | 10.00% |
| 16 | C | 0.25 | 86.00% | 14.00% |
| 17 | S | 0.25 | 86.00% | 14.00% |
| 18 | A | 0.24 | 83.00% | 17.00% |
| 19 | G | 0.25 | 86.00% | 14.00% |
| | | Average | 91.89% | 8.11% |

TABLE 9

| Calculated Resistance in Position 88 using amino acids parameter: Ra and the results of the 10 Random Sequences (R1-R10). | | | | |
|---|---|---|---|---|
| S/No | Mutant | Amplitude | Susceptibility % | Resistance % |
| 1 | I | 0.24 | 77% | 23% |
| 2 | V | 0.26 | 84% | 16% |
| 3 | F | 0.22 | 71% | 29% |
| 4 | W | 0.25 | 81% | 19% |
| 5 | L | 0.27 | 87% | 13% |
| 6 | M | 0.27 | 87% | 13% |
| 7 | A | 0.31 | 100% | 0% |
| 8 | H | 0.30 | 97% | 3% |
| 9 | E | 0.25 | 81% | 19% |
| 10 | G | 0.26 | 84% | 16% |
| 11 | C | 0.26 | 84% | 16% |
| 12 | Y | 0.23 | 74% | 26% |
| 13 | Q | 0.28 | 90% | 10% |
| 14 | T | 0.30 | 97% | 3% |
| 15 | D | 0.27 | 87% | 13% |
| 16 | R | 0.30 | 97% | 3% |
| 17 | S | 0.25 | 81% | 19% |
| 18 | N | 0.28 | 90% | 10% |
| 19 | P | 0.24 | 77% | 23% |
| 20 | K | 0.30 | 97% | 3% |
| | | Average | 86.19% | 13.81% |
| 21 | R1 | 0.12 | 39% | 61% |
| 21 | R2 | 0.17 | 55% | 45% |
| 22 | R3 | 0.15 | 48% | 52% |
| 23 | R4 | 0.01 | 3% | 97% |
| 24 | R5 | 0.07 | 23% | 77% |
| 25 | R6 | 0.00 | 0% | 100% |
| 26 | R7 | 0.06 | 19% | 71% |
| 27 | R8 | 0.03 | 10% | 90% |
| 28 | R9 | 0.07 | 23% | 77% |
| 29 | R10 | 0.07 | 23% | 77% |
| 30 | | Average | 24.3% | 75.7% |

TABLE 10

| Calculated Resistance in Position 54 using amino acids parameter: ARGP8201. | | | | |
|---|---|---|---|---|
| S/No | Mutant | Amplitude | Susceptibility % | Resistance % |
| 1 | Q | 0.29 | 100% | 0.00% |
| 2 | G | 0.28 | 100% | 0.00% |

TABLE 10-continued

Calculated Resistance in Position 54 using amino acids parameter: ARGP8201.

| S/No | Mutant | Amplitude | Susceptibility % | Resistance % |
|---|---|---|---|---|
| 3 | T | 0.28 | 100% | 0.00% |
| 4 | H | 0.29 | 100% | 0.00% |
| 5 | A | 0.29 | 100% | 0.00% |
| 6 | M | 0.30 | 100% | 0.00% |
| 7 | V | 0.30 | 100% | 0.00% |
| 8 | D | 0.30 | 100% | 0.00% |
| 9 | P | 0.31 | 100% | 0.00% |
| 10 | Y | 0.31 | 100% | 0.00% |
| 11 | I | 0.32 | 100% | 0.00% |
| 12 | W | 0.32 | 100% | 0.00% |
| | Average | | 100% | 0.00% |

In this study therefore, the tentative result of the Amprenavir-induced resistance calculated by means of the CARDC using the mutations and amino acids parameters, preliminarily studied [12] revealed, a resistance of 5.86% (Table 1). Consensus Frequency of each sequence arising from all mutations recorded against each amino acids parameter is first established. Thereafter, the amplitude of each sequence is derived. The difference between amplitude and the highest amplitude which represents the most susceptible strain of the HIV exposed to the Amprenavir is obtained as the resistance. All the Amino acids parameters are utilised and some of the results are displayed in Tables 2-10. The total resistance arising from all sequences using the amino acids parameter engaged are collated to obtain a tentative Amprenavir-induced HIV resistance of 5.86%. This therefore suggests that the drug could be recommended for this patient.

Ten (10) randomly generated sequences are analysed with the CARDC using the amino acids parameter Ra. The sequences are not analysed separately but incorporated into the dataset for amino acids parameter, Ra so as to achieve common point of interaction (CF) from which results will be derived. It is observed that the randomly generated sequences demonstrated highest resistance (75%) and also wide margin in resistance (42% and 100%) as shown in Table 9. This seems to illustrate the sensitivity, hence the reliability of the CARDC.

Also, it is revealed that some amino acids parameters displayed total susceptibility as demonstrated by ARGP8201 (Table 10). This suggests that even when all amino acids parameters are engaged, those that do not offer resistance will be identified and discarded.

In the analysis involving amino acids parameter Ra, some protein residues which are not identified in the preliminary study [12] are incorporated and analysed. It was revealed that all sequences contributed resistance. As a result, it is recommended that all sequences be analysed in order to obtain total resistance offered by the drug.

It is important to note that drug resistance can be calculated when two basic information are available. They include the mutations observed in the target proteins and the amino acids parameters engaged. Obtaining the amino acids parameters engaged requires a good knowledge of the mechanism of drug action, hence its mode of resistance. Information regarding amino acids parameters involved is difficult to obtain as mechanism s of action of most drugs have not been studied at the atomic level.

Computer-Aided Drug Resistance Calculator was preliminarily proposed to afford rationality in obtaining resistances arising from mutations in the protein residues of the target organisms [14]. This device employs a Signal Processing technique to translate protein residues into numerical numbers using appropriate amino acids parameters and further process them by means of Discrete Fourier Transform. Results obtained in this study demonstrated narrow margin. It has been recognised that more than one amino acids parameter may be involved in one mutation [12] using Amprenavir.

In this study therefore, our CARDC is applied on preliminary findings which had assessed drug activities presented by various mutations using amino acids parameters engaged so as to assess the reliability of the CARDC. Amprenavir is one drug which has been studied at the atomic level such that the amino acids parameters engaged at each mutation are identified. Amprenavir-induced Resistance on this HIV target protein, the Protease enzyme is calculated by means of the CARDC tentatively as 5.86%. This therefore appears to suggest that by this CARDC result; Amprenavir can be recommended to this patient.

Using CARDC, the Amprenavir-induced resistances in this study which have information about the mutations and amino acids parameter engaged are first obtained. The results are found to correlate with initial study [12]. The outcomes are also found promising that the CARDC is therefore further used to calculate the resistance offered to Amprenavir by the HIV that harbours mutations in its Protease enzyme as recorded in the study [12]. The tentative total resistance obtained by the CARDC is 5.86%. This appears to suggest that Amprenavir can be recommended for this patient. It is therefore demonstrated in this study that with the knowledge of mutations in the protein residues of drug targets as well as the amino acids parameter engaged, drug resistance can be calculated rather than it has being predicted.

3 REFERENCES

[1] British HIV Association (BHIVA). "Guidelines for the treatment of HIV-infected adults with antiretroviral therapy". HIV Med., 2 (2001) 4:276-313, 2001.

[2] Sension M, Cohen C J, Hunt S, et al. "A randomized trial assessing the impact of phenotypic resistance testing on antiretroviral therapy". AIDS, 16(4):579-588, 2002.

[3] Cosic I. "Macromolecular bioactivity: Is it resonant interaction between macromolecules?-theory and applications". IEEE Transactions on Biomedical Engineering, 41(I):1101-1114, 1994.

[4] Doliana R, Veljkovic V. "Emilins interact with anthrax protective antigen and inhibit toxin action in vitro". Matrix Biology, 27:96-106, 2008.

[5] Durant J, Clevenbergh P, Halfon P, et al. "Drug-resistance genotyping in hiv-1 therapy: the Viradapt randomised controlled trial". Lancet 353:219599, 1999.

[6] EuroGuidelines Group for HIV Resistance. "Clinical and laboratory guidelines for the use of HIV-1 drug resistance testing as part of treatment management: Recommendations for the European setting". AIDS, 3:309-320, 2001.

[7] Fernandez L, Caballero J, Abreu J I, et al. "Amino acid sequence autocorrelation vectors and Bayesian-regularized genetic neural networks for modeling protein conformational stability: Gene v protein mutants". PROTEINS: Structure, Function, and Bioinformatics 67:834-852, 2007.

[8] Marcelin A G, Flandre P, Chappey C, et al. Phenotypic susceptibility to Didanosine is associated with antiviral activity in treatment-experienced patients with HIV-1 infection. J Infect Dis., 195(3):392-398, 2007.

[9] Rossi M C, Gianotti N, Mondino V et al. "Comparison of a rule-based algorithm with a phenotype-based algorithm for the interpretation of HIV genotypes in guiding salvage regimens in HIV-infected patients by a randomized clinical trial: the mutations and salvage study". Clin Infect Dis., 42(10):1470-1480, 2006.
[10] Hanna G. J. and DAquila R. T. "Clinical use of genotypic and phenotypic drug resistance testing to monitor antiretroviral chemotherapy". Clin Infect Dis., 32:774-782, 2001.
[11] Schapiro J M, Brun-Vzinet F, Clotet B, et al. "Antiretroviral drug resistance testing in adult HIV-1 infection: 2008 recommendations of an International AIDS Society-USA panel". Clin Infect Dis., 47(2):266-285, 2008.
[12] Hoj L, Kjaer J, Winther O, et al. "Insilco identification of physiochemical properties at mutating position positions relevant to reducing susceptibility to Amprenavir". XVII International HIV Drug Resistance Workshop, Poster No. 113, 2008.
[13] Kapetanovic I M. "Computer-Aided Drug Discovery and Development (CADDD): in silico-chemico-biological approach". Chem Biol Interact. 171(2): 165-176, 2008.
[14] Nwankwo N, Seker H. "A signal processing-based bioinformatics approach to assessing drug resistance: Human Immunodeficiency Virus as a case study". Proc. of IEEE Eng Med Biol Soc., 2010:1836-1839, 2010.
[15] Panel on Antiretroviral Guidelines for Adults and Adolescents. "Guidelines for the use of antiretroviral agents in HIV-1-infected adults and adolescents". Department of Health and Human Services, 2011:1166, 2011.
[16] Perez-Elias M J, Garcia-Arota I, Muoz V, et al; Realvirfen study group. "Phenotype or virtual phenotype for choosing antiretroviral therapy after failure: a prospective, randomized study". Antivir Ther., 8(6):5775-84, 2003.
[17] Porter K, Babiker A, Bhaskaran K, et al; CASCADE Collaboration. "Determinants of survival following hiv-1 seroconversion after the introduction of HAART". Lancet, 362(9392):1267-1274, 2003.
[18] Brun-Vzinet F-Vandamme A Descamps D Van Laethem K Smith K et al. "HIV-1 protease and reverse transcriptase mutation patterns responsible for discordances between genotypic drug resistance interpretation algorithms". JAIDS, 33(1):8-14, 2003.
[19] Kantor R, Betts B J, Ravela J, et al. "Human Immunodeficiency Virus reverse transcriptase and protease sequence database". Nucleic Acids Research, 31(1):298-303, 2003.
[20] Thompson M A, Aberg J A, Cahn P, et al. "Antiretroviral treatment for adult HIV infection in 2002: Updated recommendations of the international aids society—usa panel". JAMA, 304(3):321-333, 2010.
[21] Regazzi M, Torti C, Quiros-Roldan E et al. "A randomized controlled trial to evaluate antiretroviral salvage therapy guided by rules-based or phenotype-driven HIV-1 genotypic drug-resistance interpretation with or without concentration-controlled intervention: the resistance and dosage adapted regimens (radar) study". Clin Infect Dis., 40(12):1828-1836, 2005.
[22] Vaidyanathan P P. "Genomics and proteomics: A signal processors tour". Proc. of IEEE Circuits and Systems Society, 4(4):6-29, 2004.
[23] Veljkovic V. and Veljkovic N. "Characterization of conserved properties of hemagglutinin of h5n1 and Human Influenza viruses: possible consequences for therapy and infection control". BMC Structural Biology, 9(21):1-11, 2009.
[24] Veljkovic V, Niman H L, Glisic S, et al. "Identification of hemagglutinin structural domain and polymorphisms which may modulate swine h1n1 interactions with human receptor". BMC Structural Biology, 9(62):1-11, 2009.
[25] Vandamme A M, Vercauteren J. "Algorithms for the interpretation of hiv-1 genotypic drug resistance information". Antiviral Res., 71(2-3):335-342, 2006.
[26] Das K, Arnold E, Petropoulos C J, et al. "A mutation in Human Immunodeficiency Virus type 1 protease, N88S, that causes in vitro hypersensitivity to Amprenavir". Journal of Virology, 74(9):4414-4419, 2000.

What is claimed is:

1. A signal processing-based bioinformatics device comprising a computer having instructions stored thereon for execution by the computer of a computational procedure for incorporating drug resistance testing into a patient management profile by performing a method to minimize drug resistance in the drug-related treatment of a patient without involving resource-consuming laboratory-based experimental procedures or predictive outcomes, comprising calculating the probability of a drug to induce resistance in a target protein utilizing a Computer-Aided Drug Resistance Calculator (CARDC) signal processing method capable of analyzing multiple amino acid parameters to calculate the total drug-induced resistance in a target protein comprising the steps of:

preparing an informational spectrum (IS), wherein preparing said informational spectrum (IS) comprises the steps of:

obtaining the consensus amino acid sequence of said target protein, identifying all drug-induced amino acid mutations of the consensus amino acid sequence of said target protein for each separate amino acid parameter, translating said consensus and mutant amino acid residues into numerical signal sequences based on the engaged parameter, and processing said numerical signal sequences to absolute values using discrete Fourier transform to prepare the informational spectrum (IS), preparing a common informational spectrum (CIS) utilizing said informational spectrum (IS) to obtain the common position of interaction by all the drug-induced mutations, by relating the discrete Fourier transform-derived amplitude and frequency values of said consensus amino acid sequence of said target protein to each of the amino acid mutations of said consensus sequence, generating a consensus frequency (CF) utilizing said common informational spectrum (CIS), calculating the level of drug resistance for each drug-induced amino acid mutation as the difference between the amplitude of each and the highest amplitude of the mutation sequences at the consensus frequency (CF), and then averaging the resistance for each set of mutations corresponding to each separate parameter, and calculating the total drug-induced resistance of said target protein to said drug by adding the average drug-induced resistance of said target protein calculated for each separate parameter, and dividing by the number of parameters, such that the calculated total drug-induced resistance is incorporated into the patient management profile, optimizing drug-related treatment to minimize drug resistance in said patient using the signal processing-based bioinformatics device.

2. The device of claim 1, wherein translating said consensus and mutant amino acid residues into numerical signal sequences is based on the alphabetic code of each amino acid residue of the engaged parameter, the information spectrum is prepared from the Fourier transform-derived amplitude and frequency values plotted, wherein the amplitude representing the level of drug resistance is the y-axis and the frequency representing the amino acid residue in the target peptide that interacts with the drug is the x-axis, and the sum total of all amplitudes equals 1.

3. The device of claim 1, wherein drug susceptibility of each drug-induced amino acid mutation is represented by the amplitude on the informational spectrum at the consensus frequency.

4. The device of claim 1, wherein said target protein is HIV-1 protease enzyme.

5. The device of claim 4, wherein 292 Amprenavir-induced amino acid mutations are identified to calculate Amprenavir-induced drug resistance in the HIV-1 protease enzyme.

6. The device of claim 5, wherein the Amprenavir-induced amino acid mutations correspond to 22 separate amino acid parameters.

7. The device of claim 1, wherein the calculated total drug-induced resistance of said target protein to said drug may be calculated by adding the average drug-induced resistance of said target protein calculated for each separate parameter, and dividing by the number of nonzero parameters.

8. A signal processing-based bioinformatics device comprising a computer having instructions stored thereon for execution by the computer of a computational procedure for incorporating drug resistance testing into a patient management profile by performing a method to minimize drug resistance in the drug-related treatment of a patient without involving resource-consuming laboratory-based experimental procedures or predictive outcomes, comprising calculating the probability of a drug to induce resistance in an HIV-1 protease protein utilizing a Computer-Aided Drug Resistance Calculator (CARDC) signal processing method capable of analyzing multiple amino acid parameters to calculate the total drug-induced resistance of an HIV-1 protease protein comprising the steps of:

preparing an informational spectrum (IS), wherein preparing said informational spectrum (IS) comprises the steps of:

obtaining the consensus amino acid sequence of said HIV-1 protease protein, identifying all drug-induced amino acid mutations of the consensus amino acid sequence of said HIV-1 protease protein for each separate amino acid parameter, translating said consensus and mutant amino acid residues into numerical signal sequences based on the engaged parameter, and processing said numerical signal sequences to absolute values using discrete Fourier transform to prepare the informational spectrum (IS), preparing a common informational spectrum (CIS) utilizing said informational spectrum (IS) to obtain the common position of interaction by all the drug-induced mutations, by relating the discrete Fourier transform-derived amplitude and frequency values of said consensus amino acid sequence of said HIV-1 protease protein to each of the amino acid mutations of said consensus sequence, generating a consensus frequency (CF) utilizing said common informational spectrum (CIS), calculating the level of drug resistance for each drug-induced amino acid mutation as the difference between the amplitude of each and the highest amplitude of the mutation sequences at the consensus frequency (CF), and then averaging the resistance for each set of mutations corresponding to each separate parameter, and calculating the total drug-induced resistance of said HIV-1 protease protein to said drug by adding the average drug-induced resistance of said target protein calculated for each separate parameter, and dividing by the number of parameters, such that the calculated total drug-induced resistance of HIV-1 protease protein is incorporated into the patient management profile, optimizing drug-related treatment to minimize drug resistance in said patient using the signal processing-based bioinformatics device.

9. The device of claim 8, wherein translating said consensus and mutant amino acid residues into numerical signal sequences is based on the alphabetic code of each amino acid residue of each of 22 parameters for Amprenavir-induced amino acid mutations, the information spectrum is prepared from the Fourier transform-derived amplitude and frequency values are plotted, wherein the amplitude representing the level of drug resistance is the y-axis and the frequency representing the amino acid residue in the HIV-1 protease protein that interacts with the drug is the x-axis, and the sum total of all amplitudes equals 1.

10. The device of claim 8, wherein the calculated total drug-induced resistance of said target protein to said drug may be calculated by adding the average drug-induced resistance of said target protein calculated for each separate parameter, and dividing by the number of nonzero parameters.

11. The device of claim 9, identifying the 292 drug-induced mutated sequences based upon said HIV-1 protease protein consensus sequence for the 22 parameters for Amprenavir-induced amino acid mutations.

12. The device of claim 8, wherein the consensus sequence is obtained from the Stanford HIV-1 resistance database.

* * * * *

SEQUENCE LISTING

```
<160> NUMBER OF SEQ ID NOS: 25

<210> SEQ ID NO 1
<211> LENGTH: 6
<212> TYPE: PRT
<213> ORGANISM: Human immunodeficiency virus

<400> SEQUENCE: 1

Val Trp Tyr Met Gln Gly
1               5


<210> SEQ ID NO 2
<211> LENGTH: 9
<212> TYPE: PRT
<213> ORGANISM: Human immunodeficiency virus

<400> SEQUENCE: 2

Ala Gly Gln Val Thr Tyr Trp Met His
1               5


<210> SEQ ID NO 3
<211> LENGTH: 11
<212> TYPE: PRT
```

-continued

```
<213> ORGANISM: Human immunodeficiency virus

<400> SEQUENCE: 3

Gln Ser Thr Val Met Trp His Tyr Cys Asn Gly
1               5                   10


<210> SEQ ID NO 4
<211> LENGTH: 16
<212> TYPE: PRT
<213> ORGANISM: Human immunodeficiency virus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 4

Gly Trp Asp Met Ala Ile Thr His Ser Xaa Gln Val Glu Tyr Cys Pro
1               5                   10                  15


<210> SEQ ID NO 5
<211> LENGTH: 12
<212> TYPE: PRT
<213> ORGANISM: Human immunodeficiency virus

<400> SEQUENCE: 5

Gln Gly Thr His Ala Met Val Asp Pro Tyr Ile Trp
1               5                   10


<210> SEQ ID NO 6
<211> LENGTH: 12
<212> TYPE: PRT
<213> ORGANISM: Human immunodeficiency virus

<400> SEQUENCE: 6

Trp Gln Tyr His Met Glu Ile Val Thr Gly Pro Ala
1               5                   10


<210> SEQ ID NO 7
<211> LENGTH: 9
<212> TYPE: PRT
<213> ORGANISM: Human immunodeficiency virus

<400> SEQUENCE: 7

Trp Pro Met Gln Val Ile Tyr Gly Asp
1               5


<210> SEQ ID NO 8
<211> LENGTH: 20
<212> TYPE: PRT
<213> ORGANISM: Human immunodeficiency virus

<400> SEQUENCE: 8

Ile Val Phe Trp Leu Met Ala His Glu Gly Cys Tyr Gln Thr Pro Arg
1               5                   10                  15

Ser Asn Pro Lys
            20


<210> SEQ ID NO 9
<211> LENGTH: 17
<212> TYPE: PRT
<213> ORGANISM: Human immunodeficiency virus

<400> SEQUENCE: 9

Met Ala Val Leu Glu Gly Lys Trp Gln Arg Phe Ser His Tyr Asp Asn
1               5                   10                  15
```

-continued

Pro

<210> SEQ ID NO 10
<211> LENGTH: 18
<212> TYPE: PRT
<213> ORGANISM: Human immunodeficiency virus

<400> SEQUENCE: 10

Trp Phe Leu Pro Met Ala Tyr Val Arg His Gln Thr Gly Ser Asn Lys
1 5 10 15

Glu Cys

<210> SEQ ID NO 11
<211> LENGTH: 14
<212> TYPE: PRT
<213> ORGANISM: Human immunodeficiency virus

<400> SEQUENCE: 11

Tyr Leu Ala Val Ile Trp His Met Ser Gln Glu Thr Cys Arg
1 5 10

<210> SEQ ID NO 12
<211> LENGTH: 15
<212> TYPE: PRT
<213> ORGANISM: Human immunodeficiency virus

<400> SEQUENCE: 12

Gly Ala Gln Thr Glu Ser Asp Cys Leu Val Phe Met Tyr His Trp
1 5 10 15

<210> SEQ ID NO 13
<211> LENGTH: 19
<212> TYPE: PRT
<213> ORGANISM: Human immunodeficiency virus

<400> SEQUENCE: 13

Thr Ser Pro Cys Arg Leu Ala Met Gly Glu Val Trp Asp Phe Tyr Asn
1 5 10 15

Gln Lys Pro

<210> SEQ ID NO 14
<211> LENGTH: 8
<212> TYPE: PRT
<213> ORGANISM: Human immunodeficiency virus

<400> SEQUENCE: 14

Val Ile Trp Glu Met Gln Asp Pro
1 5

<210> SEQ ID NO 15
<211> LENGTH: 16
<212> TYPE: PRT
<213> ORGANISM: Human immunodeficiency virus

<400> SEQUENCE: 15

Leu Ser Glu Thr Val Gly Asp Gln Phe Lys Cys Met Ile Tyr His Trp
1 5 10 15

<210> SEQ ID NO 16
<211> LENGTH: 20
<212> TYPE: PRT
<213> ORGANISM: Human immunodeficiency virus -continued

<400> SEQUENCE: 16

Trp Tyr Phe Arg Met Lys Ile Leu His Gln Val Glu Asn Pro Thr Asp
1 5 10 15

Cys Ser Ala Gly
20

<210> SEQ ID NO 17
<211> LENGTH: 8
<212> TYPE: PRT
<213> ORGANISM: Human immunodeficiency virus

<400> SEQUENCE: 17

Trp Val Tyr His Met Gln Gly Thr
1 5

<210> SEQ ID NO 18
<211> LENGTH: 7
<212> TYPE: PRT
<213> ORGANISM: Human immunodeficiency virus

<400> SEQUENCE: 18

Val Ile His Tyr Met Gln Ala
1 5

<210> SEQ ID NO 19
<211> LENGTH: 9
<212> TYPE: PRT
<213> ORGANISM: Human immunodeficiency virus

<400> SEQUENCE: 19

Gly Gln Met Trp Val Ile Tyr Glu Arg
1 5

<210> SEQ ID NO 20
<211> LENGTH: 20
<212> TYPE: PRT
<213> ORGANISM: Human immunodeficiency virus

<400> SEQUENCE: 20

Ile Val Phe Trp Leu Met Ala His Glu Gly Cys Tyr Gln Thr Pro Arg
1 5 10 15

Ser Asn Pro Lys
20

<210> SEQ ID NO 21
<211> LENGTH: 9
<212> TYPE: PRT
<213> ORGANISM: Human immunodeficiency virus

<400> SEQUENCE: 21

Gly Gln Met Trp Val Ile Tyr Glu Arg
1 5

<210> SEQ ID NO 22
<211> LENGTH: 19
<212> TYPE: PRT
<213> ORGANISM: Human immunodeficiency virus

<400> SEQUENCE: 22

Val Ile Gly Leu Glu Thr Ala Gln Ser Met Ala Tyr His Trp Asp Asn
1 5 10 15

Pro Lys Arg

<210> SEQ ID NO 23
<211> LENGTH: 99
<212> TYPE: PRT
<213> ORGANISM: Human immunodeficiency virus

<400> SEQUENCE: 23

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```

<210> SEQ ID NO 24
<211> LENGTH: 99
<212> TYPE: PRT
<213> ORGANISM: Human immunodeficiency virus N88K mutant

<400> SEQUENCE: 24

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Lys Leu Leu Thr Gln Ile Gly Cys Thr
                85                  90                  95

Leu Asn Phe
```

<210> SEQ ID NO 25
<211> LENGTH: 99
<212> TYPE: PRT
<213> ORGANISM: Artificial Sequence
<220> FEATURE:
<223> OTHER INFORMATION: Random 1 peptide

<400> SEQUENCE: 25

```
Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
```

-continued

```
65                  70                  75                  80

Asn Lys Arg Thr Gln Asp Phe Trp Glu Val Gln Leu Gly Ile Pro His
                85                  90                  95

Pro Ala Gly
```